(12) United States Patent
Taylor

(10) Patent No.: US 12,102,568 B2
(45) Date of Patent: Oct. 1, 2024

(54) FOG-REDUCING APPARATUS FOR EYE PROTECTION EQUIPMENT

(71) Applicant: Dustin Lee Taylor, Orem, UT (US)

(72) Inventor: Dustin Lee Taylor, Orem, UT (US)

( * ) Notice: Subject to any disclaimer, the term of this patent is extended or adjusted under 35 U.S.C. 154(b) by 664 days.

(21) Appl. No.: 17/227,134

(22) Filed: Apr. 9, 2021

(65) Prior Publication Data

US 2021/0315739 A1 Oct. 14, 2021

Related U.S. Application Data

(60) Provisional application No. 63/007,731, filed on Apr. 9, 2020.

(51) Int. Cl.
*A61F 9/02* (2006.01)
*A61F 9/04* (2006.01)
*A61F 9/06* (2006.01)

(52) U.S. Cl.
CPC .............. *A61F 9/028* (2013.01); *A61F 9/029* (2013.01); *A61F 9/04* (2013.01); *A61F 9/068* (2013.01)

(58) Field of Classification Search
CPC .. A61F 9/028; A61F 9/029; A61F 9/04; A61F 9/068
See application file for complete search history.

(56) References Cited

U.S. PATENT DOCUMENTS

| 1,354,433 | A | * | 9/1920 | De-Felice | G02C 11/08 2/435 |
| 2,099,464 | A | * | 11/1937 | Bruner | A61F 9/028 2/436 |
| 2,526,737 | A | * | 10/1950 | Alfred | A61F 9/028 128/201.15 |
| 3,825,953 | A | * | 7/1974 | Hunter | A61F 9/028 D16/330 |
| 4,150,443 | A | * | 4/1979 | McNeilly | A61F 9/028 2/436 |
| 9,149,391 | B1 | * | 10/2015 | Paolinetti | A61F 9/028 |
| 9,158,132 | B1 | * | 10/2015 | Cole | A61F 9/028 |
| 2009/0276940 | A1 | * | 11/2009 | Sallee | A42B 3/24 2/435 |

* cited by examiner

*Primary Examiner* — Keri J Nelson
(74) *Attorney, Agent, or Firm* — Keller Preece PLLC

(57) ABSTRACT

The present disclosure relates to a fog-reducing apparatus for eye protection equipment. For example, the fog-reducing apparatus includes a filter-pump system that provides air through one or more flexible hoses and across a lens of eye protection equipment. In certain implementations, the fog-reducing apparatus includes one or more nozzles (e.g., interchangeable nozzles) that provide directional air flow across the lens. Depending on the nozzle and/or an air flow controller, the fog-reducing apparatus can provide variable amounts of air flow and adjustable air flow direction as may be desired. In addition, the nozzle can attach to one or more components of the eye protection equipment, such as a lens, shield, or hood via one or more attachment mechanisms. Further, the nozzle can be inserted through an air vent or other hole into the eye protection equipment.

6 Claims, 9 Drawing Sheets

FOG-REDUCING APPARATUS FOR EYE PROTECTION EQUIPMENT

CROSS-REFERENCE TO RELATED APPLICATIONS

The present application claims the benefit of U.S. Provisional Application No. 63/007,731, filed on Apr. 9, 2020. The aforementioned application is hereby incorporated by reference in its entirety.

BACKGROUND

Eyewear, such as goggles or safety glasses commonly fog up during use. For example, user sweat, body heat, breathe or other sources can easily cause eyewear to fog up, thereby inhibiting use and effectiveness of the eyewear. Accordingly, there is a need for a fog-reducing apparatus that can integrate with eyewear in a convenient, efficient manner to reduce, inhibit, or prevent fog buildup on the eyewear.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY

Aspects of the present disclosure relate to a fog-reducing apparatus for eye protection equipment. For example, the fog-reducing apparatus includes a filter-pump system that provides air through one or more flexible hoses and across a lens of eye protection equipment. In certain implementations, the fog-reducing apparatus includes one or more nozzles (e.g., interchangeable nozzles) that provide directional air flow across the lens. Depending on the nozzle and/or an air flow controller, the fog-reducing apparatus can provide variable amounts of air flow and adjustable air flow direction as may be desired. In addition, the nozzle can attach to one or more components of the eye protection equipment, such as a lens, shield, or hood via one or more attachment mechanisms. Further, the nozzle can be inserted through an air vent or other hole into the eye protection equipment.

Additional features and advantages of one or more embodiments of the present disclosure are outlined in the following description.

BRIEF DESCRIPTION OF THE DRAWINGS

The detailed description provides one or more embodiments with additional specificity and detail through the use of the accompanying drawings, as briefly described below.

DETAILED DESCRIPTION

This disclosure describes one or more embodiments of a fog-reducing apparatus. In particular embodiments, the fog-reducing apparatus provides an air filter system integrable with eye protection equipment such that filtered air blows onto the eye protection equipment to limit fogging. In certain implementations, the fog-reducing apparatus includes interchangeable nozzles that provide customized air flow (e.g., adjustable direction and volume of air) onto the eye protection equipment to maintain eye comfort and fog-inhibition capabilities. In at least some embodiments, the fog-reducing apparatus can be implemented in a variety of environments and fields, such as medical and dentistry environments, foundries, factory environments, construction areas, concrete cutting areas, insulation removal/installation, mold remediation, welding, painting, agriculture, manufacturing, cleaning, automotive repair, mining, firefighting, search and rescue, military, etc.

Figure 1:
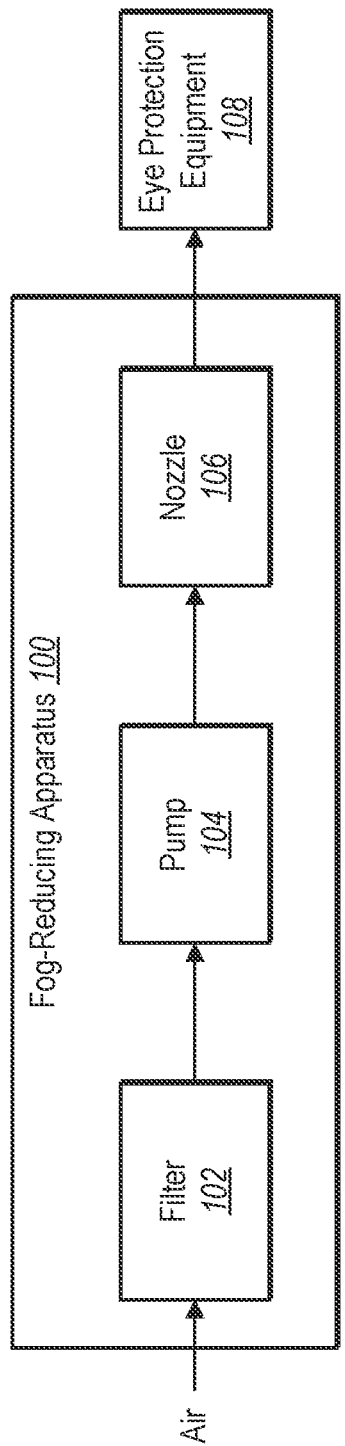
FIG. 1 illustrates a schematic diagram of a fog-reducing apparatus in accordance with one or more embodiments.

Turning to the figures, FIG. 1 illustrates a schematic diagram of a fog-reducing apparatus 100 in accordance with one or more embodiments. As shown the fog-reducing apparatus 100 provides air onto eye protection equipment 108. For example, the fog-reducing apparatus 100 circulates filtered air on or within the eye protection equipment 108 such that fog buildup is conveniently and comfortably controlled. In some embodiments, the fog-reducing apparatus 100 also introduces clean, filtered air inside the eye protection equipment 108 to increase an internal air pressure within the eye protection equipment 108 (e.g., to help keep environmental air outside of goggles, helmets, welding hoods, or other forms of the eye protection equipment 108). To do so, the fog-reducing apparatus 100 implements a variety of components. Specifically, as indicated in FIG. 1, fog-reducing apparatus 100 utilizes a filter 102, a pump 104, and a nozzle 106.

In some embodiments, the filter 102 intakes atmospheric air within the environment and outputs filtered air (e.g., by filtering particulates within the air as it passes through one or more filter components or membranes). For example, the filter 102 captures welding fumes, silica, fiberglass particles, etc. from the air intake and outputs filtered air with reduced particles. In these or other embodiments, the filter 102 can include a variety of different filters and/or filtration systems based on particle size (e.g., a P100 rating blocking particles of 0.3 microns or bigger), gas, and/or desired function. In addition, the filter 102 can include removeable/replaceable components, such as filter cartridges, membranes, meshes, coatings, covers, etc. Example types of filters for the filter 102 include, for instance, high efficiency particular air (HEPA) filters, activated carbon filters, ionic filters, electrostatic filters, ozone filters, ultraviolet filters, toxic gas filters, etc.

In some embodiments, the filter 102 pneumatically engages with the pump 104 (e.g., such that filtered air proceeds into the pump 104). In particular embodiments, the filter 102 engages with or connects to an inlet of the pump 104 (e.g., via a threaded engagement, press-fit, etc.). In some embodiments, the filter 102 comprises or else engages with one or more seals (e.g., annular seal rings to prevent air leaks by which unfiltered air bypasses the filter 102).

In addition, the pump 104 generates air suction to intake air through an inlet of the pump 104 through the filter 102 and push filtered air through an outlet of the pump 104 into a flexible tube. In some embodiments, the pump 104 comprises a variable air flow controller (e.g., that adjusts air flow between a preset volume range). Alternatively, such an air flow controller may be implemented in relation to the flexible tubing after the outlet of pump 104. Example types of pumps for the pump 104 can include micro pumps that deliver low air flow from about 1 liter to about 5 liters of air per minute.

In certain cases, the pump 104 is sufficiently strong to push filtered air through the flexible tubing (e.g., of about 1/16 inch to about 3/8 inch in diameter). Although not illustrated in FIG. 1, a variety of flexible tubing may be implemented with the pump 104. In some embodiments, the flexible tubing at the outlet of the pump 104 is larger in diameter and steps down or transitions to a smaller diameter near an opposite end of the flexible tubing connecting to the nozzle 106. Further, in some embodiments, the flexible tubing can include food grade or medical grade plastic material (e.g., with non-flammable coatings, etc.).

Additionally or alternatively, in some embodiments, the pump 104 comprises a pump housing. In certain implementations, the pump housing is sized and shaped such that an inlet and an outlet of the pump 104 are accessible from outside of the pump housing. Similarly, in some embodiments, the pump housing comprises one or more conduits for allowing a power connection (e.g., to a remote battery pack and/or one or more solar panels). For example, in some embodiments, the pump housing comprises both the pump 104 and a power source, such as interchangeable batteries or rechargeable batteries. In these or other embodiments, rechargeable batteries are rechargeable via a plug-in connection and/or via solar panels electrically coupled to the pump power source.

Additionally shown in FIG. 1, the fog-reducing apparatus 100 includes the nozzle 106. One or more embodiments of the nozzle 106 are described in further detail below in relation to FIGS. 2A-2B. In general, however, the nozzle 106 provides air onto the eye protection equipment 108. In so doing, the fog-reducing apparatus 100 can provide clean, filtered air across one or more lenses of the eye protection equipment 108 to maintain visibility and avoid fog buildup.

In some embodiments, the nozzle 106 connects to a second end of the flexible tubing opposite the first end connected to the pump 104. In this arrangement, the nozzle 106 can concentrate air flow onto the eye protection equipment 108. For example, the nozzle 106 focuses the filtered air onto the eye protection equipment 108 via specially-designed nozzle outlets that impart a particular air flow effect. Indeed, the nozzle 106 can modify the air flow from the pump 104 to provide various effects and/or air flow properties, such as a specific aim, spread, volume (or throughput), velocity, exit pressure, turbulence, laminar flow, etc. Moreover, in some embodiments, the nozzle 106 is interchangeable or adjustable to provide myriad different effects and air flow properties.

In one or more embodiments of the fog-reducing apparatus 100, the flexible tubing and/or the nozzle 106 can attach to the eye protection equipment 108 utilizing a variety of attachment mechanisms (albeit optional). Example types of attachment mechanisms include one or more of clips, clamps, Velcro® strips, elastic loops, fasteners, adhesives, fitted moldings, tube holders, snap-fits, etc. For instance, Velcro® strips can hold the flexible tubing and/or the nozzle 106 at various positions on or within the eye protection equipment 108 (e.g., inside a goggle cavity or along a headband of the eye protection equipment 108).

Alternatively, in some embodiments, the flexible tubing and/or the nozzle 106 need not attach to the eye protection equipment 108. For example, in some embodiments, the second end of the flexible tubing is inserted into an air vent or other orifice of the eye protection equipment 108 without additional contact to the eye protection equipment 108. In this embodiment, the flexible tubing and/or the nozzle 106 can naturally remain in place once inserted through the air vent or other orifice of the eye protection equipment 108. In certain implementations such as this embodiment, the fog-reducing apparatus 100 also avoids any modification to the eye protection equipment 108 (e.g., no additional holes or vents required unlike some prior art systems).

Further, in some embodiments, the nozzle 106 itself comprises an attachment mechanism for securing the nozzle 106 on or within the eye protection equipment 108. For example, in certain implementations, the nozzle 106 comprises an attachment mechanism that interfaces with one or more existing components of the eye protection equipment 108. To illustrate, in certain implementations, the nozzle 106 comprises a notch or groove configured to fit onto and hold a lens of the eye protection equipment 108.

As just described, the fog-reducing apparatus 100 can help to limit or control fog buildup on the eye protection equipment 108. In some embodiments, the eye protection equipment 108 comprises a variety of different types of eyewear/headwear. To illustrate, the eye protection equipment 108 can include, for instance, helmets, goggles, welding hoods, face shields, full-face masks, respirators, safety glasses, eye glasses, sunglasses, surgical/dental loupes, etc.

Although FIG. 1 illustrates a particular schematic of the fog-reducing apparatus 100, it can be appreciated that numerous other embodiments can be implemented. For example, in certain implementations, the fog-reducing apparatus 100 includes additional or alternative filters at different places (e.g., a pre-filter prior to the air intake, an internal filter within the pump 104, a filter within the flexible tubing, and/or a filter within the nozzle 106). As another example, in some embodiments, the fog-reducing apparatus 100 omits the nozzle 106 such that filtered air proceeds directly from a flexible tubing onto the eye protection equipment 108. In yet another example, the fog-reducing apparatus 100 includes one or more additional flexible tubings that interface with the eye protection equipment 108 (e.g., to provide additional air flow, provide safety/pressure venting, etc.). Indeed, a variety of modifications, additions, or omissions may be made to the embodiments of the fog-reducing apparatus 100 illustrated and described above in relation to FIG. 1 without departing from the scope of the present disclosure.

Figure 2A:
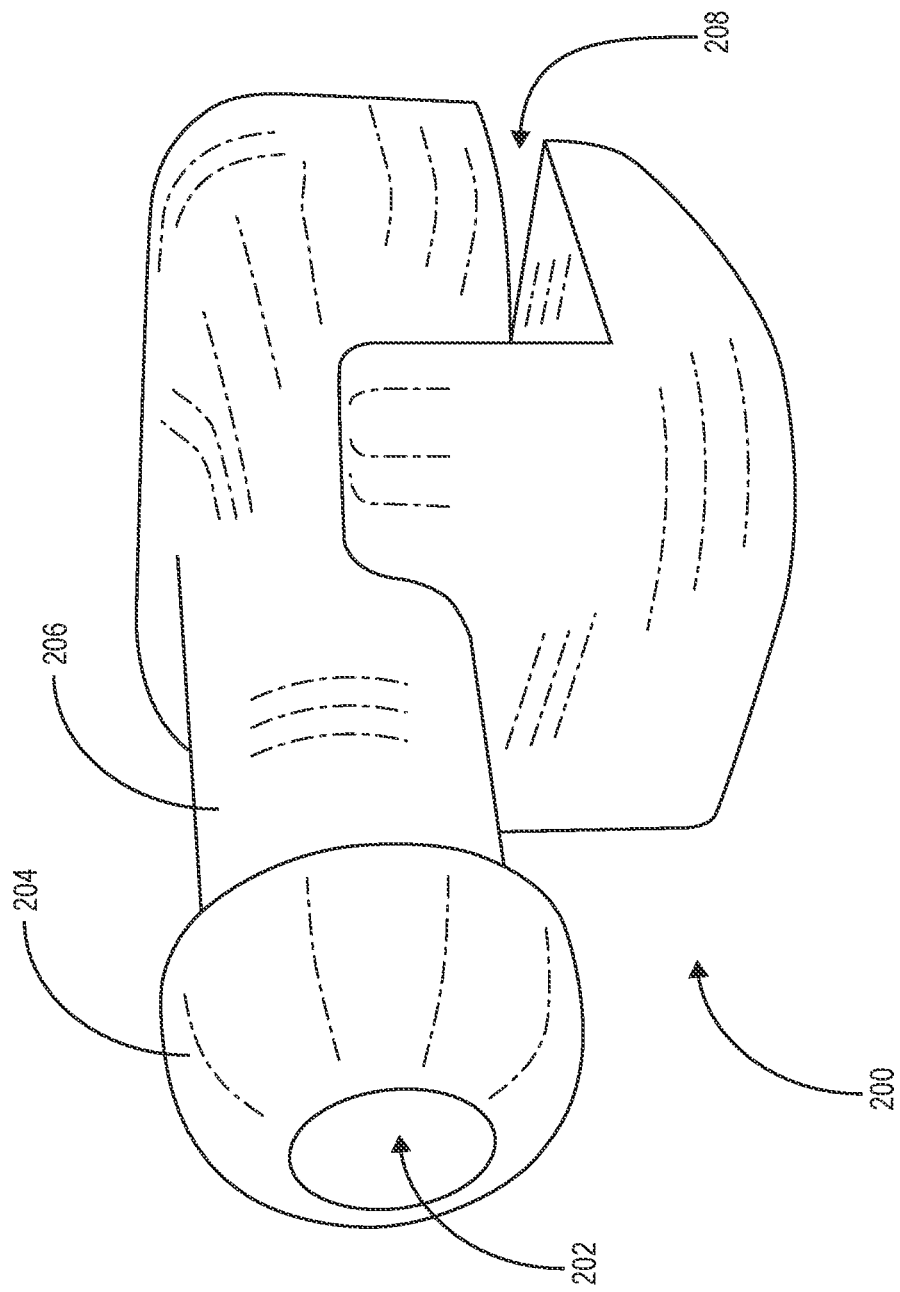
FIGS. 2A-2B illustrate a nozzle of a fog-reducing apparatus in accordance with one or more embodiments.
Figure 2B:
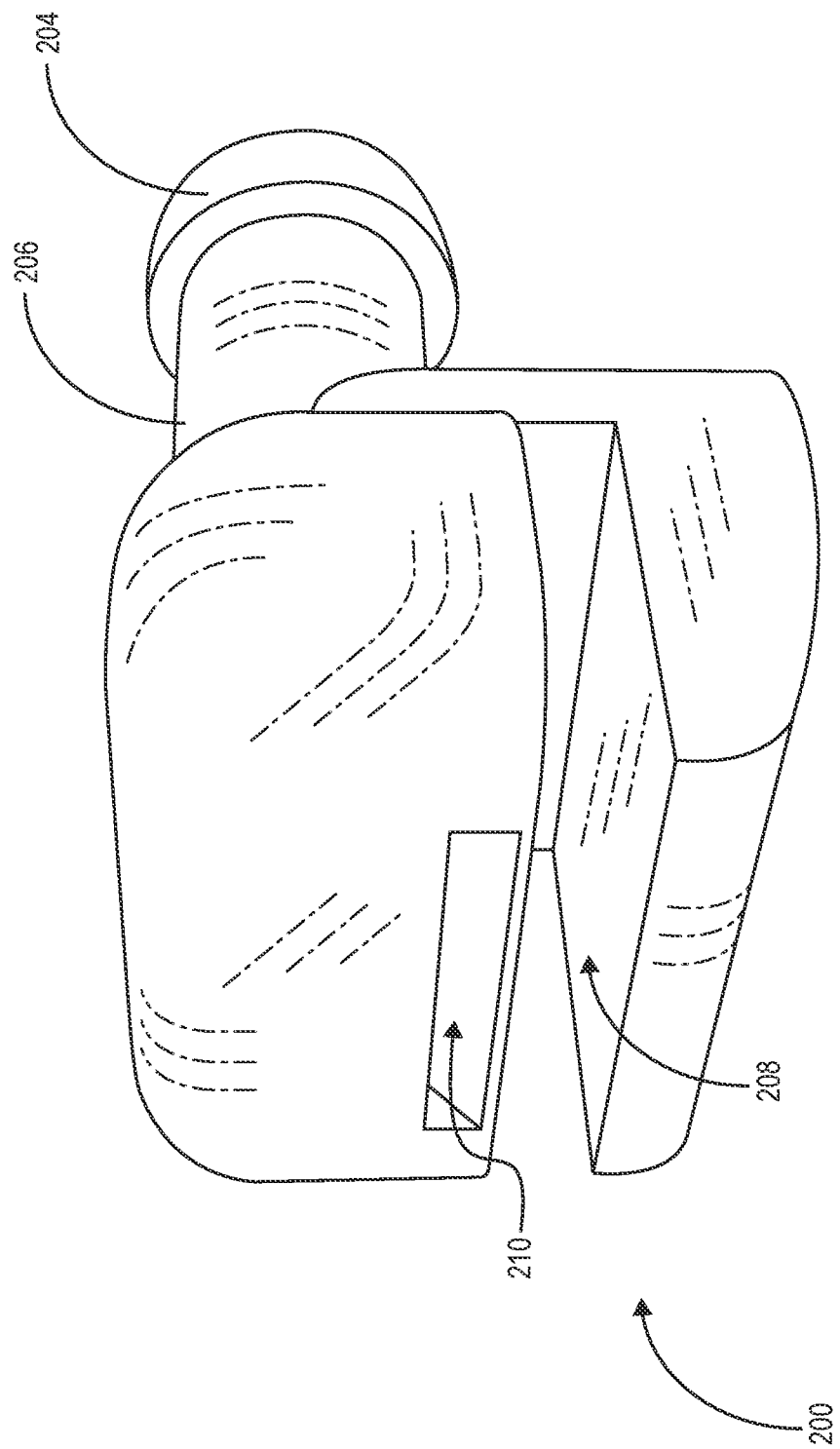
Figure 3:
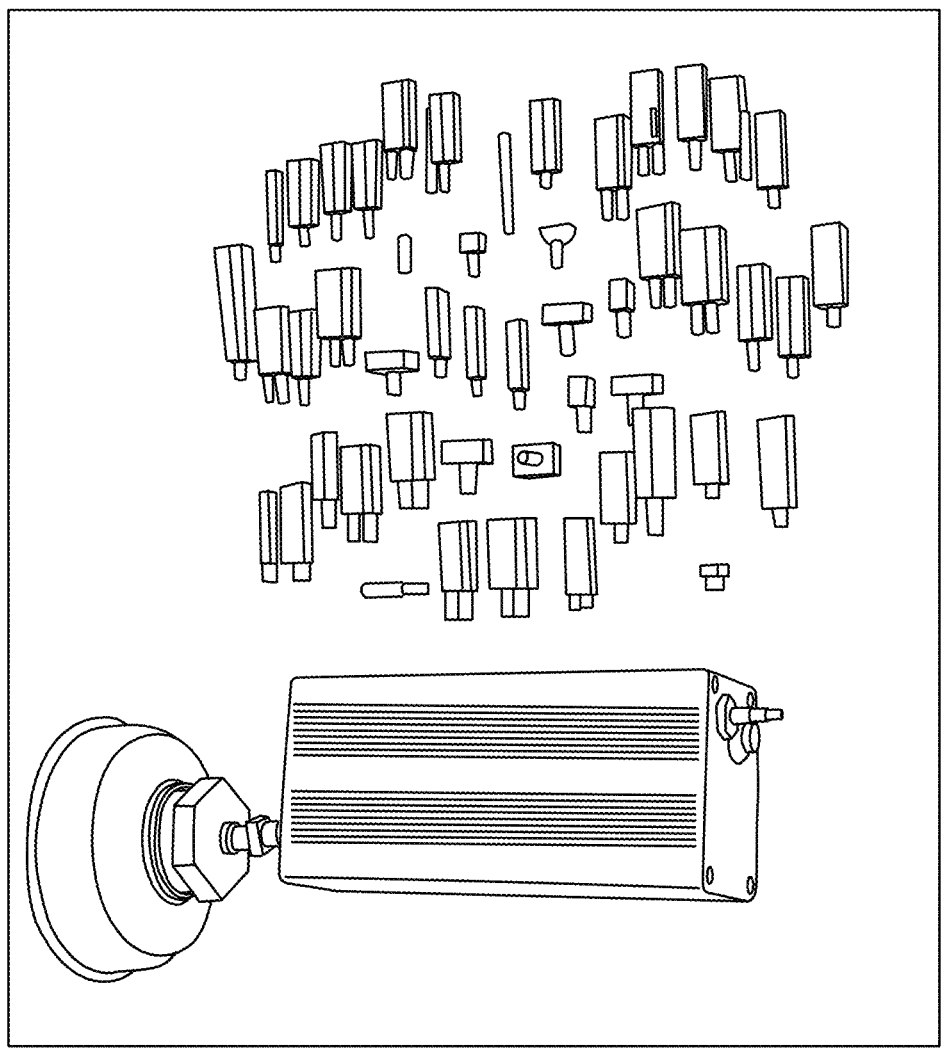
FIG. 3 illustrates components of a fog-reducing apparatus, including an air filter, an air pump, and a plurality of interchangeable nozzles in accordance with one or more embodiments.
Figure 4:
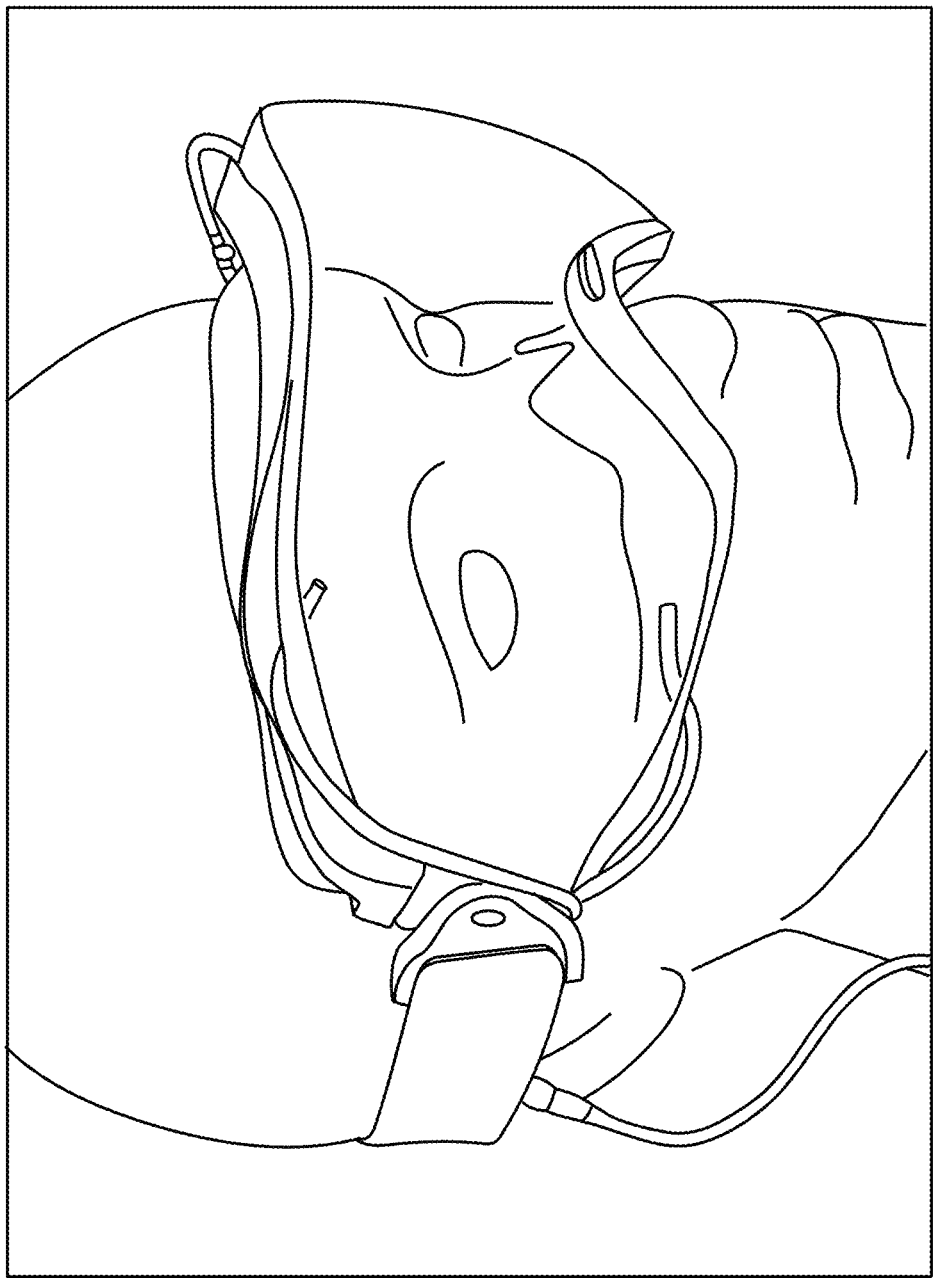
FIG. 4 illustrates components of a fog-reducing apparatus integrated with eye protection equipment in accordance with one or more embodiments.
Figure 5:
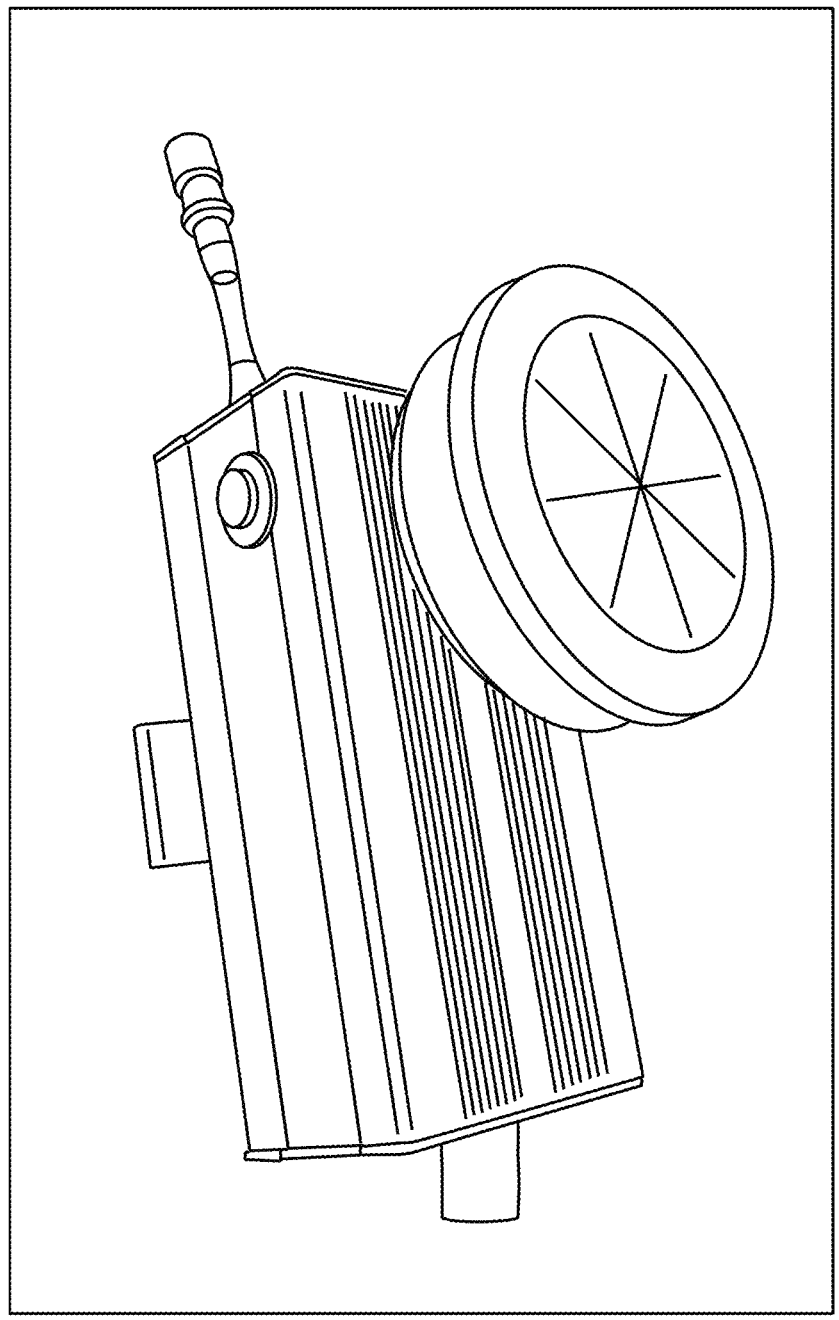
FIG. 5 illustrates components of a fog-reducing apparatus, including an air filter, an air pump, and a flexible tube in accordance with one or more embodiments.
Figure 6:
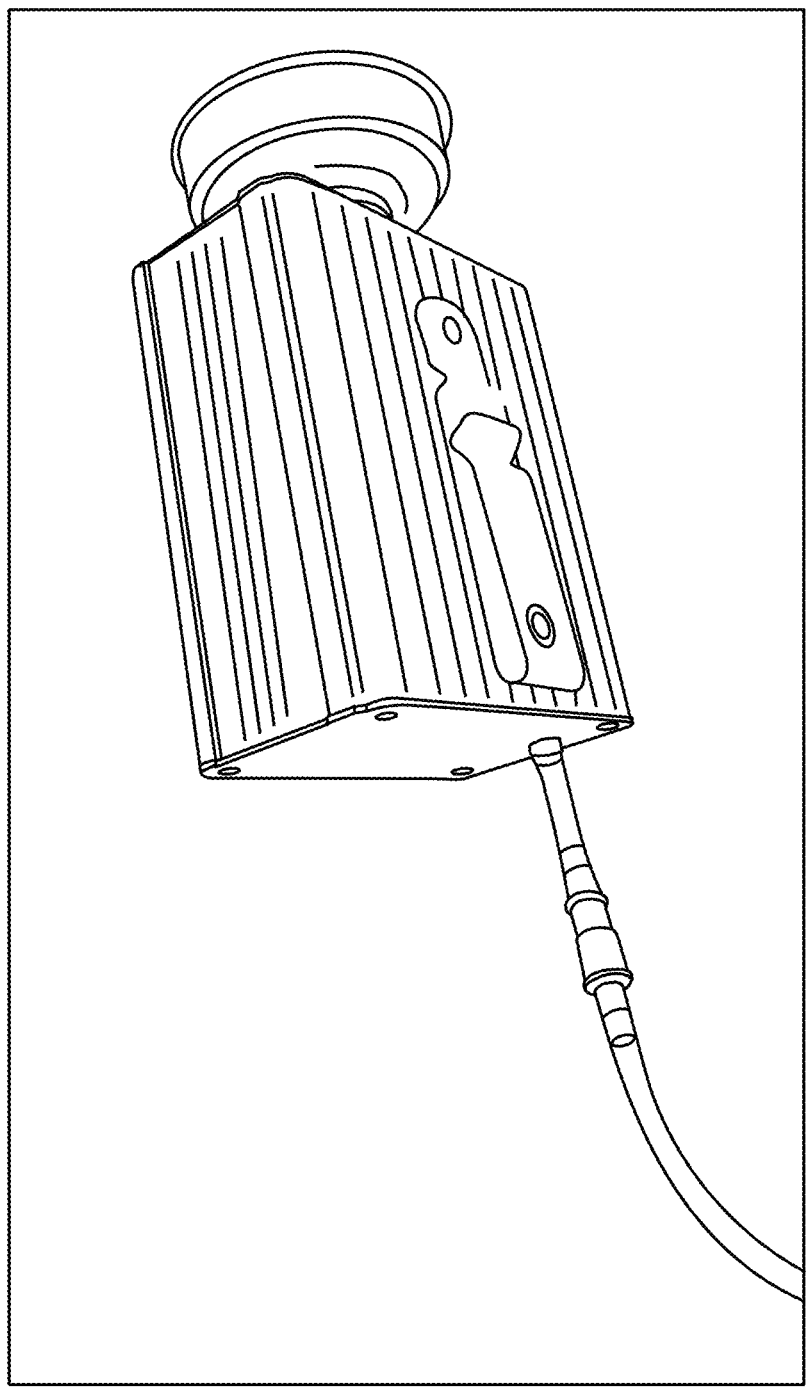
FIG. 6 illustrates components of a fog-reducing apparatus, including an air filter, an air pump, and a flexible tube in accordance with one or more embodiments.
Figure 7:
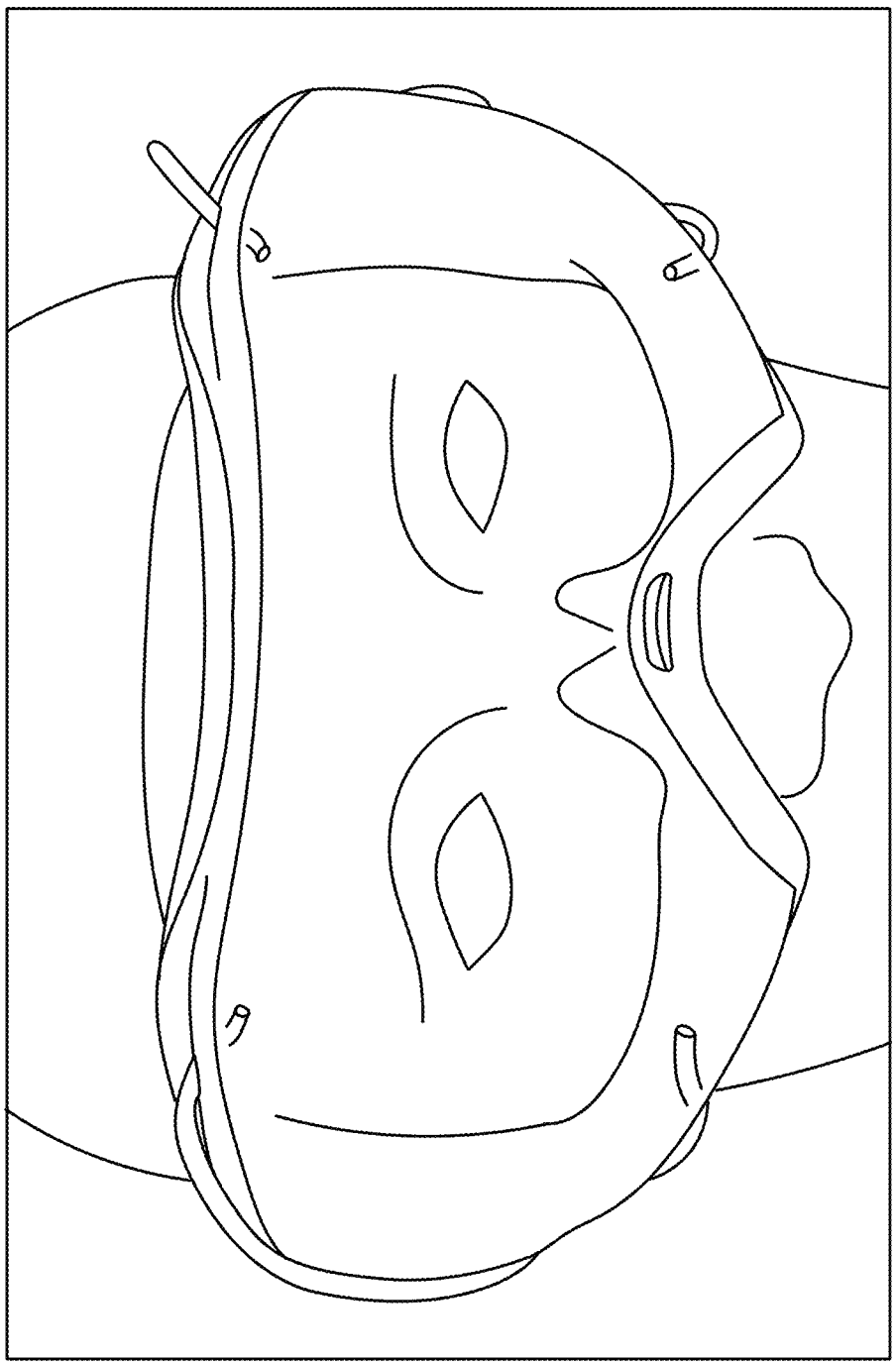
FIG. 7 illustrates components of a fog-reducing apparatus integrated with eye protection equipment in accordance with one or more embodiments.
Figure 8:
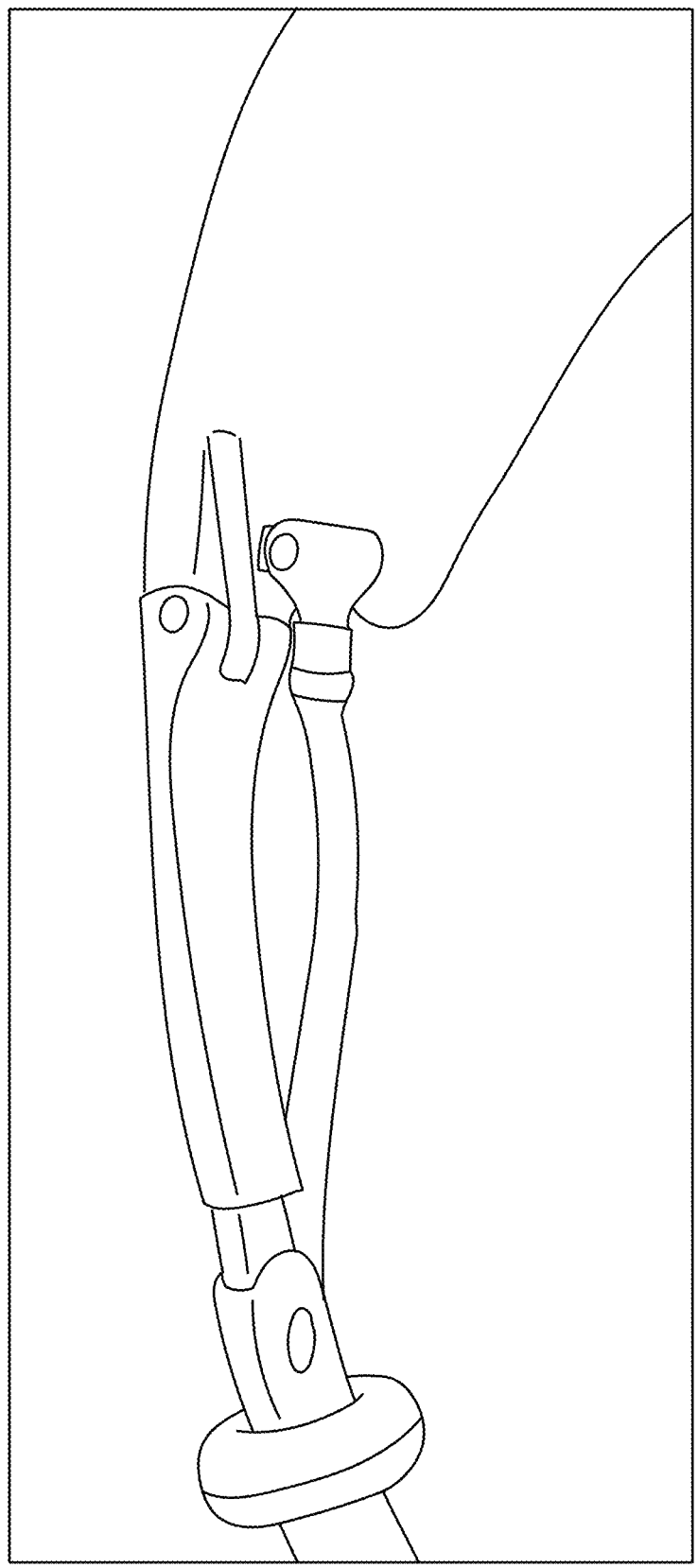
FIG. 8 illustrates components of a fog-reducing apparatus, including a flexible tube and an attachment mechanism for a nozzle integrated with eye protection equipment in accordance with one or more embodiments.

As mentioned above, the fog-reducing apparatus 100 can include a variety of different (e.g., interchangeable) nozzles that provide numerous functionalities and air flow properties for efficiently providing air onto eye protection equipment. FIGS. 2A-2B illustrate a nozzle 200 of the fog-reducing apparatus 100 in accordance with one more embodiments.

As shown, the nozzle 200 comprises a nozzle inlet 202, a head 204, a body 206, a channel 208, and a nozzle outlet 210.

In one or more embodiments, the nozzle 200 provides customized air flow onto the eye protection equipment 108. To do so, the nozzle 200 connects to flexible tubing via the head 204 and the body 206. Once the flexible tubing is fitted over the head 204 and onto the body 206, air can pass from the pump 104 through the flexible tubing and into the nozzle inlet 202.

In particular embodiments, the nozzle 200 provides customized air flow onto the eye protection equipment 108 specifically via the nozzle outlet 210. In some embodiments, the nozzle outlet 210 comprises one or more surfaces that funnel or direct filtered air out of the nozzle outlet 210 in a particular manner. To illustrate, the nozzle outlet 210 comprises a particular size and shape to impart specific air flow properties like aim, spread, volume (or throughput), velocity, exit pressure, static pressure, dynamic pressure, Reynold's number, etc. For example, although the nozzle outlet 210 is depicted as rectangular, in some embodiments, the nozzle outlet 210 is circular, triangular, square, or other polygonal shape. Additionally or alternatively, the nozzle outlet 210 (or the nozzle 200 in general) may include surface features such as ribs, bubbles, or other protrusions to impart a desired aerodynamic effect. Similarly, in some embodiments, the nozzle outlet 210 (or the nozzle 200 as a whole) may include surfaces with a particular surface roughness or surface coating to impart a desired aerodynamic effect.

As additional examples, the nozzle outlet 210 may aim air flow upwards, downwards, or at predetermined angles. Similarly, the nozzle outlet 210 may speed up air flow, throttle (or slow) air flow, concentrate air flow, or spread out air flow.

Moreover, in some embodiments, the nozzle outlet 210 can provide customized air flow for specific types of eye protection equipment. For example, the nozzle outlet 210 may provide an air flow that travels across a single lens surface or multiple lens surfaces (e.g. inside or outside lens surfaces of the eye protection equipment). Similarly, in certain implementations, the nozzle outlet 210 provides a specific air flow for the curvature of a lens (e.g., laminar flow to more closely hug a lens surface). To illustrate, the nozzle 200 may attach to a first lens of safety glasses and provide air flow to interior and/or exterior surfaces of the first lens. In this manner, the nozzle 200 can provide customized air flow onto the eye protection equipment 108 based on desired comfort and/or fog inhibition capabilities specific to the eye protection equipment 108.

As further shown, the nozzle 200 comprises the channel 208. In some embodiments, the channel 208 functions as an attachment mechanism for securing the nozzle 200 onto the eye protection equipment 108. In particular, the channel 208 includes a notch or recessed portion formed within the nozzle 200 for interfacing with a lens or other portion of the eye protection equipment 108. For example, through the channel 208, the nozzle 200 may be slidably positioned or press-fit onto a lens of the eye protection equipment 108. Additionally or alternatively, in some embodiments, the channel 208 is spring-loaded for clamping onto a lens of the eye protection equipment 108. Similarly, in certain implementations, the channel 208 includes a set screw or other fastener for securing the lens of the eye protection equipment 108 within the channel 208.

Although FIGS. 2A-2B illustrate a particular nozzle, it can be appreciated that the fog-reducing apparatus 100 can include many other nozzles. For instance, the fog-reducing apparatus 100 can implement one or more of the nozzles illustrated in the Appendix section provided below (e.g., in FIGS. A1-A11). Moreover, a nozzle of the present disclosure can include a variety of modifications, additions, or omissions may be made to the embodiments of the nozzle 200 illustrated and described above in relation to FIGS. 2A-2B without departing from the scope of the present disclosure.

In addition to the foregoing description, the present disclosure also includes the Appendix section provided below. In particular, the Appendix section provides additional illustrations in FIGS. A1-A52 depicting the fog-reducing apparatus 100 in accordance with one or more embodiments of the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A fog-reducing apparatus integrable with eye protection equipment, the fog-reducing apparatus comprising:
    an air pump comprising an inlet and an outlet;
    an air filter positioned over the inlet of the air pump;
    a first flexible tube comprising a first end and a second end, the first end in fluid communication with the outlet of the air pump;
    a first nozzle in fluid communication with the second end of the first flexible tube, the first nozzle being sized and shaped to be coupled to an upper side of an eye protection equipment and provide air flow downwards directly onto a lens of the eye protection equipment;
    a second flexible tube comprising a third end and a fourth end, the third end in fluid communication with the outlet of the air pump; and
    a second nozzle in fluid communication with the fourth end of the second flexible tube, the second nozzle being sized and shaped to be coupled to a lower side of the eye protection equipment and provide air flow upwards directly onto the lens of the eye protection equipment.

2. The fog-reducing apparatus of claim 1, wherein the first nozzle and second nozzle are interchangeable with a plurality of nozzles providing different volume amounts of air flow and directions of air flow.

3. The fog-reducing apparatus of claim 1, wherein the first nozzle and second nozzle attach to the eye protection equipment via one or more attachment mechanisms.

4. The fog-reducing apparatus of claim 1, wherein the second end of the first flexible tube is configured for inserting through an air vent into the eye protection equipment.

5. A fog-reducing apparatus integrable with eye protection equipment, the fog-reducing apparatus comprising:
    an air pump comprising an inlet and an outlet;
    an air filter positioned over the inlet of the air pump;
    a flexible tube comprising a first end and a second end, the first end connected to the outlet of the air pump;
    a first nozzle in fluid communication with the second end of the flexible tube, the first nozzle being sized and shaped to provide air flow directly onto a lens of eye protection equipment; and
    a second nozzle in fluid communication with the second end of the flexible tube, the second nozzle being sized and shaped to provide air flow upwards above the lens of the eye protection equipment.

6. A fog-reducing apparatus integrable with eye protection equipment, the fog-reducing apparatus comprising:
    an air pump comprising an inlet and an outlet;
    an air filter positioned over the inlet of the air pump;
    a first flexible tube comprising a first end and a second end, the first end in fluid communication with the outlet of the air pump;
    a first nozzle in fluid communication with the second end of the first flexible tube, the first nozzle being sized and shaped to be coupled to an upper left side of an eye protection equipment and provide air flow downwards directly onto a lens of the eye protection equipment;
    a second flexible tube comprising a third end and a fourth end, the third end in fluid communication with the outlet of the air pump;
    a second nozzle in fluid communication with the fourth end of the second flexible tube, the second nozzle being sized and shaped to be coupled to a lower left side of the eye protection equipment and provide air flow upwards directly onto the lens of the eye protection equipment;
    a third flexible tube comprising a fifth end and a sixth end, the fifth end in fluid communication with the outlet of the air pump;
    a third nozzle in fluid communication with the sixth end of the third flexible tube, the third nozzle being sized and shaped to be coupled to an upper right side of the eye protection equipment and provide air flow downwards directly onto the lens of the eye protection equipment;
    a fourth flexible tube comprising a seventh end and an eighth end, the seventh end in fluid communication with the outlet of the air pump; and
    a fourth nozzle in fluid communication with the eighth end of the fourth flexible tube, the fourth nozzle being sized and shaped to be coupled to a lower right side of the eye protection equipment and provide air flow upwards directly onto the lens of the eye protection equipment.

* * * * *